(12) United States Patent
Suzuki et al.

(10) Patent No.: US 8,986,722 B2
(45) Date of Patent: Mar. 24, 2015

(54) PEST CONTROL COMPOSITION

(75) Inventors: Takeshi Suzuki, Kamisu (JP); Takaaki Miyake, Kamisu (JP); Kazuteru Ogawa, Kamisu (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/580,032

(22) PCT Filed: Feb. 22, 2011

(86) PCT No.: PCT/JP2011/000966
§ 371 (c)(1),
(2), (4) Date: Aug. 20, 2012

(87) PCT Pub. No.: WO2011/108220
PCT Pub. Date: Sep. 9, 2011

(65) Prior Publication Data
US 2012/0316237 A1  Dec. 13, 2012

(30) Foreign Application Priority Data

Mar. 1, 2010  (JP) ................................. 2010-044151

(51) Int. Cl.
| | | |
|---|---|---|
| A01N 55/00 | (2006.01) | |
| A01N 37/00 | (2006.01) | |
| A01N 37/02 | (2006.01) | |
| A01N 37/06 | (2006.01) | |
| A01N 25/00 | (2006.01) | |
| A61K 31/21 | (2006.01) | |
| A61K 31/215 | (2006.01) | |
| A61K 31/22 | (2006.01) | |
| A61K 31/225 | (2006.01) | |
| A61K 31/23 | (2006.01) | |
| A01N 37/36 | (2006.01) | |

(52) U.S. Cl.
CPC ................ A01N 37/06 (2013.01); A01N 37/36 (2013.01)
USPC ............. 424/405; 514/63; 514/506; 514/529; 514/547; 514/549; 514/552

(58) Field of Classification Search
None
See application file for complete search history.

(56) References Cited

U.S. PATENT DOCUMENTS

| | | | | |
|---|---|---|---|---|
| 4,112,083 | A * | 9/1978 | Hurt ............................... | 514/126 |
| 5,912,208 | A | 6/1999 | Hioki et al. | |
| 6,294,578 | B1 | 9/2001 | Arimoto et al. | |
| 2002/0142021 | A1* | 10/2002 | Matsuo et al. ................. | 424/405 |
| 2003/0049362 | A1 | 3/2003 | Hori et al. | |
| 2005/0261133 | A1 | 11/2005 | Nakanishi et al. | |
| 2006/0165748 | A1 | 7/2006 | Arimoto | |
| 2007/0135329 | A1* | 6/2007 | Wang et al. .................... | 510/466 |
| 2008/0171686 | A1 | 7/2008 | Takewaki et al. | |
| 2008/0214713 | A1 | 9/2008 | Hasebe et al. | |
| 2011/0028521 | A1* | 2/2011 | Morita et al. .................. | 514/355 |
| 2011/0111961 | A1* | 5/2011 | Sun ............................... | 504/323 |

FOREIGN PATENT DOCUMENTS

| | | | |
|---|---|---|---|
| EP | 0765602 | A1 | 4/1997 |
| EP | 0862861 | A1 | 9/1998 |
| EP | 1645187 | A1 | 4/2006 |
| JP | 5-345702 | A | 12/1993 |
| JP | 10-251104 | A | 9/1998 |
| JP | 11-1404 | A | 1/1999 |
| JP | 11-29411 | A | 2/1999 |
| JP | 11-29413 | A | 2/1999 |
| JP | 2001-226205 | A | 8/2001 |
| JP | 2001-316206 | A | 11/2001 |
| JP | 2002-226311 | A | 8/2002 |
| JP | 2002226311 | A * | 8/2002 |
| JP | 2002-294286 | A | 10/2002 |
| JP | 2004-262971 | A | 9/2004 |
| JP | 2005-29489 | A | 2/2005 |
| JP | 2005-41873 | A | 2/2005 |
| JP | 2005-336266 | A | 12/2005 |
| JP | 2005-344076 | A | 12/2005 |
| JP | 2005-350360 | A | 12/2005 |
| JP | 2008-169176 | A | 7/2008 |
| JP | 2008-239563 | A | 10/2008 |
| JP | 2009-40747 | A | 2/2009 |
| WO | 00/27195 | A1 | 5/2000 |
| WO | 2008/117875 | A1 | 10/2008 |
| WO | WO 2009128409 | A1 * | 10/2009 |

OTHER PUBLICATIONS

International Search Report and Written Opinion mailed May 31, 2011 in corresponding PCT application No. PCT/JP2011/000966.
International Preliminary Report on Patentability mailed Sep. 13, 2012 in corresponding PCT application No. PCT/JP2011/000966.
Extended European Search Report mailed Jul. 5, 2013 (completed Jun. 27, 2013) in corresponding European patent application No. EP 11750334.2.
Emalex Products HLB List, Jan. 1, 2001, XP 55068043A, http://www.nihon-emulsion.co.jp/english/products/hlblist.html, 9 pages, Nihon Emulsion Co., Ltd.

(Continued)

Primary Examiner — Juliet Switzer
Assistant Examiner — Caralynne Helm
(74) Attorney, Agent, or Firm — Nields, Lemack & Frame, LLC

(57) ABSTRACT

It is an object of the present invention to provide a pest control composition capable of exerting a high effect on pests such as spider mites and aphids even at low concentration using a food/food additive with high safety to the human body and the environment. The present inventors have intensively studied to solve the above problem and found that, among polyglycerol fatty acid esters widely used as a food additive, a composition containing a polyglycerol fatty acid ester which has an HLB of 5 or less and is liquid at ordinary temperature and also a nonionic surfactant has a high effect on pests even at low concentration, and that the possibility for pests to develop resistance to the composition is extremely low, and the present invention has been completed.

20 Claims, No Drawings

(56) References Cited

OTHER PUBLICATIONS

Emalex DSG-3—Triglyceryl Distearate, Jan. 1, 2001, XP 55068047A, http://www.nihon-emulsion.co.jp/english/products/list/E-DSG-3.htm, 1 page, Nihon Emulsion Co., Ltd.

Glycerol Monooleate, Processing, Sep. 25, 2001, pp. 1-16, XP 55067972A, http://www.ams.usda.gov/AMSv1.0/getfile?dDocName=STELPRDC5057603, NOSB TAP Review Compiled by OMRI.

Sy-Glyster Properties, Product Specifications, Jan. 1, 2001, pp. 1-3, XP 55068104A, http://www.sy-kogyo.co.jp/english/sei/1_sy_list.html, Sakamoto Yakuhin Kogyo Co., Ltd.

Arlacel 481, 986, 1689 & 1690, Mar. 1, 2009, pp. 1-4, XP 55068427A, http://www.innovadex.com/documents/995937.pdf?bs=1409&b=36916&st=20, Croda Europe, Ltd.

European communication dated Jul. 21, 2014 in corresponding European patent application No. EP 11750334.2.

Science and Industry, vol. 63(2), 1989, pp. 65-72, "Development and Industrialization of Polyglycerol Ester of Fatty Acids", Yamashita, et al.

Journal of the Japanese Society for Food Science and Technology, Nippon Shokuhin Kagaku Kogaku Kaishi, vol. 50, No. 11, 2003, pp. 537-545, "Studies on Growth Characteristics of *Bacillus* Strains Isolated from a Liquid Seasoning", Nakayama, et al.

Japanese communication, with English translation, mailed Nov. 4, 2014 in corresponding Japanese patent application No. 2012-502994.

\* cited by examiner

PEST CONTROL COMPOSITION

TECHNICAL FIELD

The present invention relates to a pest control composition. More specifically it relates to a pest control composition for agricultural and horticultural crops, where polyglycerol fatty acid ester is an effective main component.

BACKGROUND ART

In order to stably provide agricultural and horticultural crops, it is essential to control insect pests and diseases. At present, in order to control those diseases and pests, synthetic agrochemicals are widely used due to their excellent economic efficiency and control effect. However, if synthetic agrochemicals are continuously used, their target pests develop resistance to synthetic agrochemicals in some cases. In addition, recently, consumers' consciousness of agrochemicals has been raised, so there is a requirement for an agrochemical which is highly safe to the human body and the environment.

In such a situation, in recent years, pest control compositions having an action mechanism different from synthetic agrochemicals are reported.

Patent Literature 1 discloses a pest control agent containing a water-soluble polymer as an effective component, and discloses that said pest control agent may further contain a surfactant selected from dialkyl sulfosuccinate-based surfactants, silicone-based surfactants, acetylene glycol-based surfactants, polycarboxylic acid-based surfactants and alkylbenzene sulfonic acid salts. This control agent is described as a pest control agent which physically suffocate pests to death so as to control them by spraying onto small pests such as spider mites and aphids injurious to vegetables or fruit trees, directly or after dilution with water 50 to 100 times. In addition, it is described that water-soluble polymer concentration is 100 to 10000 ppm and preferably 500 to 5000 ppm in terms of the effective component concentration, but it is disclosed that in the examples, the control test was carried out on mites using a diluent having a water-soluble polymer concentration of 2000 ppm or 5000 ppm. However, when spraying is carried out at such a high concentration, there is a concern about chemical injury to target crops caused thereby. Further, due to its low dilution factor, preparation of a diluent with water is frequent and cumbersome, and thus worse workability is raised as a problem.

Patent Literature 2 discloses an insecticidal and bactericidal agent for agriculture and horticulture with an effective component being a triglyceride consisting of middle chain fatty acid, which has 8 to 10 carbon atoms, and discloses that it can be mixed with a suitable surfactant or carrier. In addition, Patent Literature 2 describes that the triglyceride consisting of middle chain fatty acid, which have 8 to 10 carbon atoms has a special penetration ability into the skin of small harmful insects such as spider mites, aphids, broad mites, thripses and whiteflies, due to which it is inferred to break the balance of the body fluid, leading to their death, and describes that said insecticidal and bactericidal agent is a composition which physically acts to control.

However, Patent Literature 2 does not describe the effective component concentration in a spray liquid, and in the examples, the above-described insecticidal and bactericidal agent was used at a high concentration to some extent. Specifically, an example is described in which said composition was diluted with water 100 to 500 times and sprayed at an effective component concentration of 1800 ppm, 2250 ppm, 4500 ppm or 9000 ppm. In the case of spraying at such a high concentration, the large amount of the pest control agent to be used and the cumbersome operation of preparing the diluent are raised as problems. In addition, there is a concern about chemical injury to target crops because the middle chain fatty acid triglyceride having a relatively high hydrophobicity is used at a high concentration.

Patent Literature 3 discloses an insecticidal and acaricidal composition containing a certain fatty acid ester and a non-ionic surfactant, and describes that said combination has high insecticidal and acaricidal effects compared with other fatty acid esters. More specifically, it discloses an insecticidal and acaricidal composition containing a combination of at least one kind of fatty acid ester selected from the group consisting of glycerol monooleate, glycerol monolinoleate, glycerol monocaprylate, glycerol mono or dioleate, glycerol di or trioleate, glycerol mono or .dilinoleate, glycerol mono or diricinoleate, glycerol diacetomonolaurate, sorbitan laurate, sorbitan oleate, diglycerol laurate, diglycerol oleate, diglycerol monolaurate, diglycerol monooleate, tetraglycerol oleate, hexaglycerol laurate, decaglycerol laurate, propylene glycol monolaurate and propylene glycol monoleate, with a nonionic surfactant. With regard to this composition, it is described that the effective component concentration in a diluent is preferably 0.02 to 10% by weight. It is described that in the examples, said composition was effective on two-spotted spider mites with a water-diluted liquid at a low concentration as an effective component concentration of 70 to 90 mg/100 ml by diluting 1000 times, while it is disclosed that in a test example, said composition was effective on cotton aphids, greenhouse whiteflies and thripses at a concentration of 140 to 180 mg/100 ml as an effective component concentration by diluting 500 times. Accordingly, it is a problem that said insecticidal and acaricidal composition is found to have significant difference in control efficacy between target pest species.

RELATED TECHNICAL LITERATURE

Patent Literature

Patent Literature 1: Japanese Patent Laid-Open No. H7-126105 A

Patent Literature 2: Japanese Patent Laid-Open No. H11-29411 A

Patent Literature 3: Japanese Patent Laid-Open No. H10-251104 A

SUMMARY OF THE INVENTION

Problems to be Solved by the Invention

A pest control agent having a starch or a fatty acid derivative as an effective component according to the conventional techniques generally requires a high concentration spray of an effective component. For this reason, it is a problem that the diluent preparation operation is cumbersome and there is a concern about causing chemical injury to crops. In addition, it requires a large amount of pest control agent for spray and thus has a disadvantage in the cost. Further, it is raised as a problem that it has a difference in control efficacy between target insect pests, and there has been a desire for a pest control agent capable of simultaneously controlling a plural species of pests by one spray of a low concentration dilute solution of the control agent.

It is an object of the present invention to provide a pest control agent capable of achieving control of agricultural and horticultural pests at low concentration with an effective component ensuring safety to humans. In addition, it is to provide a pest control agent having no difference in control effect between target pest species. Particularly, it is to provide a pest control agent, in a low concentration spray, having sufficient control efficacy on both of spider mites and aphids which are agriculturally important pests.

Means of Solving the Problems

The present inventors have intensively studied to solve the above problems, focused on polyglycerol fatty acid ester which is widely used as a food additive and found that a polyglycerol fatty acid ester having an HLB of 5 or less and being liquid at ordinary temperature has a high effect on pests in agriculture and horticulture even at a low concentration, and the present invention has been completed.

That is, the present invention relates to an invention constituting the below-described (1) to (19).

(1) A pest control composition containing a polyglycerol fatty acid ester having an HLB of 5 or less and being liquid at ordinary temperature, and a nonionic surfactant.
(2) The pest control composition according to the above-described (1), wherein the polymerization degree of the polyglycerin in the polyglycerol fatty acid ester is 6 to 10.
(3) The pest control composition according to the above-described (1) or (2), wherein the constituent fatty acid of the polyglycerol fatty acid ester contains omega-9 fatty acid of unsaturated fatty acid.
(4) The pest control composition according to the above-described (1) or (2), wherein the constituent fatty acid of the polyglycerol fatty acid ester contains one kind or two kinds or more selected from the group consisting of oleic acid, erucic acid and ricinoleic acid.
(5) The pest control composition according to any one of the above-described (1) to (4), wherein the esterification rate of the polyglycerol fatty acid ester is 70% or more.
(6) The pest control composition according to any one of the above-described (1) to (5), wherein the polyglycerol fatty acid ester is at least one selected from the group of hexaglycerol pentaoleate, decaglycerol decaoleate, decaglycerol erucate and polyglycerol condensed ricinoleate.
(7) The pest control composition according to any one of the above-described (1) to (6), wherein the nonionic surfactant is a nonionic surfactant having a surface tension (20° C.) of 23 mN/m or less and an HLB of 13 or more in a 0.1% by mass aqueous solution.
(8) The pest control composition according to any one of the above-described (1) to (7), wherein the nonionic surfactant is a polyether-modified organopolysiloxane.
(9) The pest control composition according to any one of the above-described (1) to (8), wherein the content of the polyglycerol fatty acid ester is 30 to 98% by mass and the content of the nonionic surfactant is 2 to 30% by mass in the composition.
(10) The pest control composition according to any one of the above-described (1) to (9), wherein the composition is an emulsion to control a pest in agriculture and horticulture.
(11) The pest control composition according to any one of the above-described (1) to (10), wherein the pest is one kind or two kinds or more of organisms belonging to the animal order selected from the group consisting of Acarina, Hemiptera and Thysanoptera.
(12) A spray liquid obtained by diluting the pest control composition according to any one of the above-described (1) to (10) with water.
(13) A method for controlling a pest, which is characterized in that the spray liquid according to the above-described (12) is directly sprayed onto a pest or a crop at which a pest is emerging.
(14) The method for controlling a pest according to the above-described (13), where the polyglycerol fatty acid ester concentration in a spray liquid is 300 to 2000 ppm.
(15) The method for controlling a pest according to the above-described (13) or (14), wherein the pest is one kind or two kinds or more of organisms belonging to the animal order selected from the group consisting of Acarina, Hemiptera and Thysanoptera.
(16) The pest control composition according to the above-described (1), wherein:
the polyglycerol fatty acid ester is a polyglycerol fatty acid ester in which the polymerization degree of the glycerin is 2 to 10, the fatty acid of the fatty acid ester is a C8 to C24 fatty acid having at least one unsaturated bond in the aliphatic chain, the esterification rate of the hydroxy group in the polyglycerin is 60 to 100% and the HLB is 0 to 5;
the nonionic surfactant is a nonionic surfactant having an HLB of 12 or more and a surface tension of 30 mN/m or less at 20° C. in a 0.1% by mass solution;
the content of said polyglycerol fatty acid ester is 30 to 98% by mass, the content of said nonionic surfactant is 2 to 40% by mass, and the total content of said polyglycerol fatty acid ester and said nonionic surfactant is 40 to 100% by mass, based on the total amount of the composition; and
the rest 0 to 60% by mass is an arbitrary additional component;
the pest is a pest in agriculture and horticulture; and
the composition is an emulsion.
(17) The pest control composition according to the above-described (1) or (16), wherein:
the nonionic surfactant is a polyether-modified organopolysiloxane having an HLB of 12 or more, the content is 2 to 35% by mass, and the total content of the above polyglycerol fatty acid ester and said nonionic surfactant is 50 to 100% by mass, based on the total amount of the composition; and
the rest 0 to 50% by mass is an arbitrary additional component, and said additional component is at least one kind selected from the group consisting of nonionic surfactants other than the above polyether-modified organopolysiloxane, anionic surfactants, animal and vegetable oils which are a liquid at ordinary temperature and water-soluble solid carriers.
(18) The pest control composition according to the above-described (17), wherein any either or both of the nonionic surfactant other than the above polyether-modified organopolysiloxane or the anionic surfactant is 0 to 30% by mass, the animal and vegetable oils which are a liquid at ordinary temperature is 0 to 50% by mass, and the total of the above surfactant and the above animal and vegetable oils is 0 to 50% by mass, based on the total amount of the composition.
(19) The pest control composition for agriculture and horticulture according to Claim 1, wherein:
the constituent fatty acid of the above polyglycerol fatty acid ester is at least one kind selected from the group consisting of oleic acid, erucic acid and ricinoleic acid;
the above nonionic surfactant is a polyether-modified organopolysiloxane; and
in the composition, the content of the above polyglycerol fatty acid ester is 30 to 98% by mass and the content of said nonionic surfactant is 2 to 30% by mass, and the arbitrary additional component is 0 to 60% by mass.

Effect of the Invention

The pest control composition of the present invention exhibits an excellent control effect on pests, particularly small pests such as spider mites and aphids of agricultural and horticultural crops and also its effective component is a polyglycerol fatty acid ester having a track record of being used as a food additive and ensuring safety to the human body, so the pest control composition of the present invention is extremely highly safe. In addition, the pest control composition of the present invention can control pests at lower concentration compared with a known composition. For this reason, the risk of chemical injury to agricultural crops can be mitigated. Further, said pest control composition has a sufficient pest control effect even when used in a small amount and therefore also has an advantage in the cost. Furthermore, its diluent preparation is easy and thus it can improve workability. In addition to that, said pest control composition exhibits an excellent control effect on different kinds of small pests such as spider mites and aphids and also in each stage of larva, nymph, adult and the like and can be applied for controlling a variety of small pests, and also it allows simultaneous control of these plural pests by one spray.

MODE FOR CARRYING OUT THE INVENTION

The present invention has been completed based on the finding that a pest control composition containing, as an effective component, a polyglycerol fatty acid ester which has an HLB of 5 or less and is liquid at ordinary temperature and also containing a nonionic surfactant (hereinafter, which is also referred to as "the pest control composition of the present invention" or "the present invention composition" in the present description) exhibits a more excellent control effect than in the case where another fatty acid ester is used as an effective component.

In the present description, the "pest control composition" refers to a composition directly acting on small insect pests (which is also referred to as small pest) such as spider mites and aphids and controlling by, for example, inhibiting the movement of small pests, blocking the spiracle of small organisms or doing the like leading to physical pest death.

In the present description, "liquid at ordinary temperature" means a liquid having flowability at 20° C.

Determination of a liquid having flowability at 20° C. is made in accordance with the fluid confirmation test specified in 2 of Article 69 in Japanese "Rules for Regulations on Dangerous Substances".

The specific method for the fluid confirmation test is as described below.

Preparing a flat-bottomed cylindrical type glass-made test tube having an internal diameter of 30 mm and a height of 120 mm, lines (A line and B line) are drawn on the positions 55 mm and 85 mm high from the bottom of the test tube. At a temperature of 20° C. and under atmospheric pressure, an object is put to the height of the A line of said test tube perpendicularly placed, and then said test tube is horizontally laid. The time elapsed since said test tube is horizontally laid until the top of the moving surface of the object passes the B line is measured, and determination of the liquid is made when the time is 90 seconds or less (20° C.). It is preferred that the above-described time of the polyglycerol fatty acid ester of the present invention is 5 seconds or less (20° C.).

The HLB (Hydrophile-Lipophile Balance) is an index indicating degrees of hydrophilic properties and lipophilic properties of a surfactant and being shown by a numerical value of 0 to 20. A low HLB indicates that a surfactant has higher lipophilic properties and a high HLB indicates that a surfactant has high hydrophilic properties. Therefore, a surfactant having a low HLB is apt to adapt to a hydrophobic system and a surfactant having a high HLB is apt to adapt to a hydrophilic system. In short, it is said that the index shows which system of water/oil systems the surfactant is easily mixed into.

As the HLB value of said polyglycerol fatty acid ester, a numerical value derived from the following calculation method which is an empirical formula by Griffin is applied. In this regard, as the below-described saponification and acid values, values analyzed in accordance with general test procedures of standards for food additives and standards of quasi-drug ingredients are used.

$$\text{HLB value} = 20(1 - S/A)$$

S: Saponification value for an ester of a surfactant.
A: Acid value of a fatty acid constituting a surfactant.

The polyglycerol fatty acid ester having an HLB of 5 or less and being liquid at ordinary temperature which is used in the present invention (hereinafter, which is also referred to as "said polyglycerol fatty acid ester" in the present description) is a substance used as a food additive, and widely used as an emulsifier for whipped cream, coffee whitener, margarine, shortening, chocolate, milk beverage, functional fats and oils, and the like can be used. For this reason, the pest control composition of the present invention has, as a main component, a raw material ensuring safety of intake in humans.

The polyglycerol fatty acid ester used for the present invention is a fatty acid ester in which a plurality of fatty acids are bonded to a polyglycerin having 2 or more of a chain length (polymerization degree) of the glycerin.

The polyglycerol fatty acid ester being liquid at ordinary temperature and having an HLB of 5 or less which is used for the present invention includes, for example, the following ones: diglycerol dioleic acid ester (HLB: about 4), diglycerol trioleic acid ester (HLB: about 3), diglycerol tetraoleic acid ester (HLB: about 2), tetraglycerol trioleic acid ester (HLB: about 5), tetraglycerol tetraoleic acid ester (HLB: about 4), tetraglycerol pentaoleic acid ester (HLB: about 2), tetraglycerol hexaoleic acid ester (HLB: about 2), hexaglycerol pentaoleic acid ester (HLB: about 5), hexaglycerol hexaoleic acid ester (HLB: about 4), hexaglycerol heptaoleic acid ester (HLB: about 4), hexaglycerol octaoleic acid ester (HLB: about 4), decaglycerol heptaoleic acid ester (HLB: about 5), decaglycerol octaoleic acid ester (HLB: about 5), decaglycerol nonaoleic acid ester (HLB: about 4), decaglycerol decaoleic acid ester (HLB: about 4), decaglycerol undecaoleic acid ester (HLB: about 3), decaglycerol dodecaoleic acid ester (HLB: about 3), decaglycerol erucic acid ester (HLB: about 3.5), or polyglycerol-condensed ricinoleic acid ester such as hexaglycerol-condensed ricinoleic acid ester (HLB: about 3).

The polyglycerol fatty acid esters described above are commercially available as the names of SY Glyster (which is a trade name and manufactured by Sakamoto Yakuhin Kogyo Co., Ltd.) and the like.

The HLB of said polyglycerol fatty acid ester is preferably 5 or less and the lower limit thereof is 0 or more. In the present invention, the polyglycerol fatty acid ester is not particularly limited as long as having an HLB of 0 to 5. The HLB is preferably 2 to 5 and more preferably 3 to 5.

On the other hand, when a polyglycerol fatty acid ester having an HLB of 10 or more (on the hydrophilic side) is contained as a main effective component, the sufficient efficacy is not exerted on spider mites and aphids in a spray test at low concentration, as shown in Comparative Example mentioned later.

For example, when hexaglycerol monooleic acid ester (HLB: about 11), decaglycerol monocapric acid ester (HLB: about 16), diglycerol monooleic acid ester (HLB: about 8) or tetraglycerol monolauric acid ester (HLB: about 10) is contained as a main effective component, a very preferable effect is not shown.

However, in the present application, it is not excluded that these components are contained in the present invention composition as other additives.

As the polyglycerol fatty acid ester used for the present invention, any ester can be used as long as it is an ester of a polyglycerin having a polymerization degree of 2 or more with a fatty acid, has an HLB in the above-described range and is liquid at ordinary temperature. As a polyglycerol fatty acid ester more effectively exerting the control effect on target pests, a polyglycerol fatty acid ester having a polyglycerin polymerization degree of 2 to 20, preferably 4 to 12 and more preferably of 6 to 10 is desired.

As the constituent fatty acid of the polyglycerol fatty acid ester used for the present invention, any of saturated or unsaturated fatty acids can be used. The carbon atom number of said constituent fatty acid is preferably 8 to 30, more preferably 12 to 24 and further preferably 16 to 24.

As said constituent fatty acid, an unsaturated fatty acid having one or more unsaturated bonds in the fatty acid chain is preferable. Said unsaturated fatty acid preferably includes omega-3 fatty, omega-6 fatty or omega-9 fatty acids having one unsaturated bond and a carbon atom number of 8 to 24. In addition, among these unsaturated fatty acids, omega-9 fatty acid is preferable. The typical omega-9 fatty acid of these unsaturated fatty acids can include omega-9 fatty acids having a carbon atom number of 18 to 24 and specifically includes oleic acid, erucic acid and ricinoleic acid (preferably condensed ricinoleic acid). These fatty acids are preferable as a fatty acid constituent said polyglycerol fatty acid ester effectively exerting the control effect on target pests.

The number of the bonding fatty acid in said polyglycerol fatty acid ester is not particularly limited as long as the HLB of said polyglycerol fatty acid ester is within the above-described range, but it is preferably 60% or more and more preferably 70% or more in terms of esterification rate (the rate of the hydroxy group esterified with a fatty acid based on the total number of the hydroxy group in the polyglycerin) of the hydroxy group the polyglycerin has.

The polyglycerol fatty acid ester having a esterification rate of 70% or more includes diglycerol tetraoleic acid ester (esterification rate: 100%), tetraglycerol pentaoleic acid ester (esterification rate: 83%), tetraglycerol hexaoleic acid ester (esterification rate: 100%), hexaglycerol hexaoleic acid ester (esterification rate: 75%), hexaglycerol heptaoleic acid ester (esterification rate: 88%), hexaglycerol octaoleic acid ester (esterification rate: 100%), decaglycerol nonaoleic acid ester (esterification rate: 75%), decaglycerol decaoleic acid ester (esterification rate: 83%), decaglycerol undecaoleic acid ester (esterification rate: 92%), decaglycerol dodecaoleic acid ester (esterification rate: 100%) and the like.

Preferable specific examples of said polyglycerol fatty acid ester include hexaglycerol hexaoleic acid ester, hexaglycerol heptaoleic acid ester, hexaglycerol octaoleic acid ester, decaglycerol heptaoleic acid ester, decaglycerol octaoleic acid ester, decaglycerol nonaoleic acid ester, decaglycerol decaoleic acid ester, decaglycerol undecaoleic acid ester, decaglycerol dodecaoleic acid ester, decaglycerol erucic acid ester, or polyglycerol-condensed ricinoleic acid ester such as hexaglycerol-condensed ricinoleic acid ester, and it is more preferably hexaglycerol pentaoleic acid ester, decaglycerol decaoleic acid ester, decaglycerol erucic acid ester or polyglycerol-condensed ricinoleic acid ester (for example, hexaglycerol-condensed ricinoleic acid ester) and particularly preferably decaglycerol decaoleate.

Said polyglycerol fatty acid esters can be used alone and also 2 kinds or more of the polyglycerol fatty acid esters can be mixed to use.

Preferable said polyglycerol fatty acid esters are listed as follows.

(i) An polyglycerol fatty acid ester being liquid at ordinary temperature and having an HLB of 2 to 5.

(ii) The polyglycerol fatty acid ester according to the above-described (i), wherein the HLB is 3 to 5.

(iii) The polyglycerol fatty acid ester according to the above-described (i) or (ii), wherein the polyglycerin polymerization degree is 2 to 20.

(iv) The polyglycerol fatty acid ester according to the above-described (iii), wherein the polyglycerin polymerization degree is 6 to 10.

(v) The polyglycerol fatty acid ester according to any one of the above-described (i) to (iv), wherein the carbon atom number of the fatty acid constituent the polyglycerol fatty acid ester (hereinafter, which is referred to as said constituent fatty acid) is 8 to 30.

(vi) The polyglycerol fatty acid ester according to the above-described (v), wherein said fatty acid is an unsaturated fatty acid having one unsaturated bond and a carbon atom number of 8 to 24.

(vii) The polyglycerol fatty acid ester according to the above-described (vi), wherein said constituent fatty acid is an omega-9 fatty acid having a carbon atom number of 18 to 24.

(viii) The polyglycerol fatty acid ester according to the above-described (vii), wherein said constituent fatty acid is at least one selected from the group consisting of oleic acid, erucic acid and ricinoleic acid.

(ix) The polyglycerol fatty acid ester according to the above-described (viii), wherein the ricinoleic acid is condensed ricinoleic acid.

(x) The polyglycerol fatty acid ester according to any one of the above-described (i) to (ix), wherein the esterification rate of the polyglycerol fatty acid ester is 70% or more.

(xi) The polyglycerol fatty acid ester according to any one of the above-described (i) to (iv), wherein the polyglycerol fatty acid ester is at least one selected from the group of hexaglycerol pentaoleic acid ester, decaglycerol decaoleic acid ester, decaglycerol erucic acid ester and polyglycerol-condensed ricinoleic acid ester.

(xii) The polyglycerol fatty acid ester according to the above-described (xi), wherein the polyglycerol-condensed ricinoleic acid ester is hexaglycerol-condensed ricinoleic acid ester.

(xiii) The polyglycerol fatty acid ester according to the above-described (i), wherein the polyglycerol fatty acid ester is decaglycerol decaoleate.

The content of the polyglycerol fatty acid ester in the pest control composition in the present invention is suitably 30 to 98% by mass, preferably 35 to 95% by mass, more preferably 50 to 90% by mass and most preferably 70 to 90% by mass. In the case where the content of the polyglycerol fatty acid ester is too low, the control effect on harmful insect pests is not sufficient when it is diluted at low concentration, and on the contrary, in the case of the too high content, sufficient suspension in water cannot be conducted in dilution with water due to the too small amount of a surfactant to be used. The present invention composition contains said polyglycerol fatty acid ester as an effective component in a high content and therefore allows less frequent operation for preparation of a spray liquid by dilution with water, thus providing good handling.

The pest control composition of the present invention requires use of a nonionic surfactant in order to sufficiently exert the control effect of said polyglycerol fatty acid ester on target pests.

As a nonionic surfactant used in the pest control composition of the present invention (hereinafter, which is also referred to as "said nonionic surfactant"), any nonionic surfactant usually used for agrochemical formulations can be used. A preferable nonionic surfactant used in combination with said polyglycerol fatty acid ester in the present invention can include nonionic surfactants (hereinafter which is also referred to as polyether nonionic surfactant) having a polyC2-C4 (preferably C2-C3) alkylene ether group. Specific examples thereof include, for example, nonionic surfactants such as polyoxyethylene alkyl ether, a polyoxyethylene polyoxypropylene copolymer, polyoxyethylene alkylaryl ether, polyoxyethylene styrylphenyl ether, a polyoxyethylene phenyl ether polymer, polyoxyethylene alkylene aryl phenyl ether, a polyoxyethylene polyoxypropylene block polymer, and polyether-modified organopolysiloxane. Among these, polyether-modified organopolysiloxane is more preferable as said nonionic surfactant because it shows an excellent pest control effect in combination use with said polyglycerol fatty acid ester.

As the nonionic surfactant used in the present invention, they can be used alone or 2 kinds or more thereof can be mixed to use.

The HLB range of said nonionic surfactant is usually 11 to 20 (11 to 18 in some cases), preferably 12 to 20 and more preferably approximately 12 to 18. It is further preferably 13 or more.

In addition, the surface tension (20° C., 0.1% by mass aqueous solution) of said nonionic surfactant is usually 32 mN/m or less, further preferably 30 mN/m or less and most preferably 23 mN/m or less. Further, the lower limit of said surface tension is not particularly limited but preferably it is usually 18 mN/m or more. Therefore, the range of said surface tension is suitably 18 to 30 mN/m and most suitably 18 to 23 mN/m.

Said nonionic surfactant in which said surface tension is 18 to 30 mN/m and the HLB is 12 to 18 is more preferable.

Among these nonionic surfactants, a nonionic surfactant having a surface tension of 23 mN/m or less in a 0.1% by mass aqueous solution (20° C.) and an HLB of 13 or more is particularly preferable because the effect of effectively controlling target insect pests is excellent in application by spraying the present invention composition diluted with water.

A polyether-modified organopolysiloxane satisfying the above-described range of HLB and surface tension is a more preferable nonionic surfactant in the present invention.

For surface tension in the present description, a numerical value measured by Wilhelmy method (plate method) is used. The principle of measurement is as described below. When a platinum plate is contacted with the surface of a liquid, the liquid rises along the plate. Then, surface tension acts along the periphery of the plate and a force drawing the plate into the liquid is generated. Thus in the method, this drawing force is measured and the surface tension is measured. Specifically, a 0.1% by mass aqueous solution of a sample nonionic surfactant is made as a measurement sample, which is measured by an automatic surface tension measuring machine (for example, DY-300 automatic surface tension meter, manufactured by Kyowa Interface Science Corp., Ltd.) by Wilhelmy method shown above at a temperature of 20° C. to determine the surface tension. With regard to the value of the surface tension measured in such a method, low tensile strength indicates that the drawing force at the surface is low, suggesting that the "intermolecular force" between molecules of the liquid is weak. The nonionic surfactant has a property to decrease the surface tension of an aqueous solution. For this reason, when an aqueous solution containing this adheres to the surface of another substance, "wettability" at said surface is improved. As a result, a diluent of the present invention composition containing said nonionic surfactant easily adheres to the surface of target pests and the surface of spray-target agricultural crops.

To the HLB of the nonionic surfactant in the present description, a value derived by the following method using a calculation formula of Griffin which is known as a calculation formula for HLB values regarding fatty acid ester of polyhydric alcohol is applied.

HLB value=$E/5$

E: Weight fraction of the alkylene oxide group (preferably, ethylene oxide group) in a surfactant.

Said nonionic surfactant, preferably the nonionic surfactant in the above preferable range of HLB and surface tension (for example, the HLB is 12 or more and the above surface tension is 30 mN/m or less) can be quickly dissolved with water when diluted with water, leading to an enhanced effect of spreading water on the surface of crops onto which its diluent is sprayed. On the other hand, said nonionic surfactant tends to have low ability of micellizing said polyglycerol fatty acid ester in a water-diluted liquid. For the reason, the water-diluted liquid of the present invention composition has a tendency that the micelle of said polyglycerol fatty acid ester in water is fragile. As a result, the micelle of the present invention composition in a water-diluted liquid is in an unstable state such that association or the like easily occurs. For the reason, the polyglycerol fatty acid ester having an HLB value of 5 or less which is an effective component of the pest control composition of the present invention increasingly tends to aggregate to an object with high hydrophobicity. By utilizing this phenomenon, spraying the present invention composition diluted with water facilitates aggregation and adhesion of said polyglycerol fatty acid ester to a surface of target insect pests with high hydrophobicity. Said polyglycerol fatty acid ester tends to efficiently adhere around the spiracle of target insect pests above all, so actions such as blocking the spiracle with said polyglycerol fatty acid ester are easily exerted and it is possible to achieve effective physical control.

That is, with regard to the combination of said polyglycerol fatty acid ester and said nonionic surfactant, a composition having a combination of compounds with low compatibility to each other surprisingly exhibits a more superior pest control effect.

Therefore, in the present invention composition, the combination of said polyglycerol fatty acid ester and said nonionic surfactant (preferably polyether nonionic surfactant in which the HLB is 12 or more and the above-described surface tension is 30 mN/m or less, particularly polyether-modified organopolysiloxane) is preferable.

The polyether-modified organopolysiloxane as said nonionic surfactant is preferably polyC2-C4 alkyl ether-modified polyC1-C3 alkyl polysiloxane. In said polyether-modified organopolysiloxane, the polymerization degree of the polyether is approximately 2 to 40 and preferably approximately 2 to 10 as an average value, and the polymerization degree of the polysiloxane is 2 to 20, preferably approximately 2 to 10 and more preferably approximately 3 to 10 as an average value.

An example of said preferable polyether-modified organopolysiloxane is shown in a structural formula as described below.

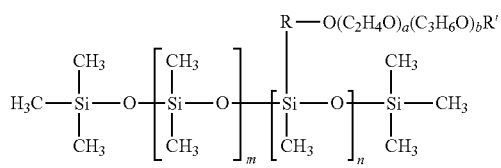

m+n (polysiloxane polymerization degree): 1 to 10, m=0 to 9, n=1 to 10,
a (ethylene oxide polymerization degree): 1 to 20,
b (propylene oxide polymerization degree): 0 to 20,
R is an oxygen atom or a C1-C4 alkylene group, and
R' is a C1 to C4 alkyl group which may be substituted by a phenyl.

A more preferable polyether-modified organopolysiloxane is preferably one having a surface tension (20° C.) and/or an HLB in a 0.1% by mass aqueous solution which are included in the preferable range described above. In addition, the polyether-modified organopolysiloxane represented by the above-described structural formula is preferably one in which the polysiloxane polymerization degree m+n is 1 to 5, m is 0 to 4, n is 1 to 5, the ethylene oxide polymerization degree a is 1 to 10, and the propylene oxide polymerization degree b is 0 to 5.

In this regard, 2 kinds or more of the polyether-modified organopolysiloxane can be used by mixing to prepare one adjusted to the above physical properties.

The polyether-modified organopolysiloxane used for the present invention is generally commercially available and can be easily obtained from the market. For example, KF-640 (which is a trade name and manufactured by Shin-Etsu Chemical Co., Ltd.; HLB: 13.5, surface tension: 21 mN/m), KF-643 (which is a trade name and manufactured by Shin-Etsu Chemical Co., Ltd.; HLB: 14, surface tension: 21 mN/m), KF-351A (which is a trade name and manufactured by Shin-Etsu Chemical Co., Ltd.; HLB: 12, surface tension: 26 mN/m) and the like are commercially available, and these commercial products can be used. Or, 2 kinds or more thereof can be mixed to use.

A more preferable nonionic surfactant in the present invention is one having such physical properties that the surface tension (20° C.) in a 0.1% by mass aqueous solution is 23 mN/m or less (for example, 20 to 23 mN/m) and the HLB is 13 or more (for example, 13 to 15). The polyether-modified organopolysiloxane corresponding to these physical properties includes the above KF-640 and KF-643. Polyether-modified organopolysiloxanes can be mixed to prepare a polyether-modified organopolysiloxane corresponding to the above physical properties, which can be also used.

A combination of the above-described polyether-modified organopolysiloxane having a more preferable surface tension and HLB with the above polyglycerol fatty acid ester having an HLB of 5 or less is a more preferable combination in the present invention.

In the present invention composition, the content of said nonionic surfactant is usually 2 to 40% by mass, preferably 2 to 35% by mass, more preferably 2 to 30% by mass and further preferably 5 to 30% by mass. In addition, 10 to 20% by mass is the most preferable in some cases.

In this regard, in the present description, the expression "the content in the composition of the present invention" means a ratio based on the total amount of the present invention composition in any case unless otherwise specifically described.

The contents of the polyglycerol fatty acid ester and the nonionic surfactant in the present invention composition can be arbitrarily varied in the range allowing the polyglycerol fatty acid ester to sufficiently exert the physical control effect on target insect pests. To make a composition having an efficient control effect, a composition in which 30 to 98% by mass of the polyglycerol fatty acid ester and 2 to 30% by mass of the nonionic surfactant are contained in said composition is preferable, and a composition in which 35 to 95% by mass of the polyglycerol fatty acid ester and 5 to 20% by mass of the nonionic surfactant are contained is more preferable.

In addition, when the total content of the polyglycerol fatty acid ester and the nonionic surfactant is usually 50 to 100% by mass, preferably 60 to 100% by mass, and further preferably 70 to 100% by mass based on the total amount of the present invention composition, the present invention composition exerts a more excellent pest control effect.

Further, in the present invention, the preferable content ratio of the polyglycerol fatty acid ester and the nonionic surfactant is a ratio in which, based on 1 part by mass of the nonionic surfactant (preferably, polyether nonionic surfactant, more preferably polyether-modified organopolysiloxane), the polyglycerol fatty acid ester is usually 2 to 20 parts by mass, preferably 2 to 10 parts by mass, more preferably 3 to 8 parts by mass and further preferably 3 to 7 parts by mass.

The pest control composition of the present invention can contain an arbitrary additional component within the range not eliminating the excellent physical control effect in the present invention. For example, as said additional component, any additional component which may be used for emulsions can be used. Specifically, additional components such as anionic surfactants, animal and vegetable oils which are liquid at ordinary temperature or water-soluble solid carriers can be used. In addition, when the nonionic surfactant as an essential component in the present invention is, for example, a polyether nonionic surfactant, a polyether-modified organopolysiloxane, or the like having an HLB of 12 or more, nonionic surfactants other than the nonionic surfactant as said essential component (hereinafter, which is referred to as nonionic surfactant as an arbitrary component) are included in the arbitrary components.

The above-described anion-based surfactant is not particularly limited as long as generally used in agrochemicals and includes, for example, sodium dialkylsulfosuccinate, polyoxyethylene styrylphenyl ether sulfate, ligninsulfonic acid salts, alkylarylsulfonic acid salts, alkylnaphthalenesulfonic acid salts, calcium stearoyl lactylate and the like. The anion-based surfactant can be used within the range of 0 to 15% by mass and preferably 0 to 10% by mass based on the present invention composition.

The total content of the above-described said anion-based surfactant and the nonionic surfactant as the above-described arbitrary component is usually 0 to 30% by mass based on the total amount of the present invention composition.

The above-described animal and vegetable oils which are liquid at ordinary temperature are preferably animal and vegetable oils generally used in foods, food additives, agrochemicals and the like. They include, for example, vegetable oils which are liquid at ordinary temperature, such as raw sesame oil, sesame oil, soybean oil and rapeseed oil, and raw sesame oil is more preferable. The animal and vegetable oils which are liquid at ordinary temperature, more preferably raw sesame oil, can be used within the range of 0 to 50% by mass and preferably 0 to 40% by mass based on the present invention composition.

The above-described water-soluble solid carrier includes porous dextrin and the like.

The content of these arbitrary additional components is in the range of 0 to 60% by mass and preferably within the range of 0 to 40% by mass, and in some cases, 0 to 30% by mass, based on the total amount of the present invention composition.

In addition, the total content of any either or both of the nonionic surfactant or the anionic surfactant as the above-described arbitrary component and the above animal and vegetable oils based on the total amount of the present invention composition is preferably approximately 0 to 50% by mass and more preferably within the range of 0 to 40% by mass, and in some cases, 0 to 30% by mass.

The formulation of the pest control composition of the present invention is preferably a formulation which substantially contains no water and is oily at ordinary temperature, and usually an emulsion (emulsifiable concentrate).

Preferable aspects (embodiments) of the pest control composition of the present invention will be exemplified below. In this regard, % represents "% by mass".

(I) A pest control composition containing 30 to 98% of the polyglycerol fatty acid ester having an HLB of 5 or less and being liquid at ordinary temperature, 2 to 30% of said nonionic surfactant and 0 to 60% of an arbitrary additional component, based on the total amount of the present invention composition.

(II) The pest control composition according to the above-described (I), wherein the content of said polyglycerol fatty acid ester is 35% to 95% and the content of said nonionic surfactant is 5 to 30%.

(III) The pest control composition according to the above-described (II), wherein the content of said nonionic surfactant is 5 to 20%.

(IV) The pest control composition according to any one of the above-described (I) to (III), wherein the total content of said polyglycerol fatty acid ester and said nonionic surfactant is 50 to 100% based on the total amount of the present invention composition, and the rest is an arbitrary additional component.

(V) The pest control composition according to the above-described (I), wherein the content of said polyglycerol fatty acid ester is 50% to 90%, the content of said nonionic surfactant is 10 to 30%, the rest is an arbitrary additional component, and the total content of said polyglycerol fatty acid ester and said nonionic surfactant is 60 to 100%.

(VI) The pest control composition according to any one of the above-described (I) to (III), wherein the content of said polyglycerol fatty acid ester is 70% to 90%, the content of said nonionic surfactant is 10 to 25%, and the rest is an arbitrary additional component.

(VII) The pest control composition according to any one of the above-described (I) to (V), wherein the total content of said polyglycerol fatty acid ester and said nonionic surfactant is 70 to 100% based on the total amount of the present invention composition, and the rest is an arbitrary additional component.

(VIII) The pest control composition according to any one of the above-described (I) to (VII), wherein said polyglycerol fatty acid ester is the polyglycerol fatty acid ester according to any one of the above (i) to (xiii).

(IX) The pest control composition according to any one of the above-described (I) to (VIII), wherein the HLB of the nonionic surfactant is 11 to 20.

(X) The pest control composition according to the above-described (IX), wherein said HLB is 12 or more.

(XI) The pest control composition according to the above-described (X), wherein said HLB is 12 to 18.

(XII) The pest control composition according to the above-described (X) or (XI), wherein said HLB is 13 or more.

(XIII) The pest control composition according to any one of the above-described (IX) to (XII), wherein the surface tension (20° C.) of said nonionic surfactant in a 0.1% by mass aqueous solution is 18 to 30 mN/m.

(XIV) The pest control composition according to any one of the above-described (IX) to (XIII), wherein said nonionic surfactant is a polyether nonionic surfactant.

(XV) The pest control composition according to any one of the above-described (IX) to (XIV), wherein said nonionic surfactant is a polyether-modified organopolysiloxane.

(XVI) The pest control composition according to the above-described (XV), wherein the polyether-modified organopolysiloxane is a polyC2-C4 alkyl ether-modified polyC1-C3 alkyl polysiloxane.

(XVII) The pest control composition according to the above-described (XV) or (XVI), wherein the polymerization degree of the polyether is approximately 2 to 40 as an average value and the polymerization degree of the polysiloxane is 2 to 20 as an average value in the polyether-modified organopolysiloxane.

(XVIII) The pest control composition according to any one of the above-described (X) to (XVII), wherein when said nonionic surfactant is the nonionic surfactant according to any one of the above-described (X) to (XVII), at least one kind of arbitrary components selected from the group consisting of nonionic surfactants, anionic surfactants, animal and vegetable oils and water-soluble solid carriers as an arbitrary additional component may be contained corresponding to each thereof.

(XIX) The pest control composition according to the above-described (I) or (XVIII), wherein the nonionic surfactant is a polyether-modified organopolysiloxane having an HLB of 12 or more, the content thereof is 2 to 35% by mass based on the total amount of the composition, the total content of the above polyglycerol fatty acid ester and said nonionic surfactant is 50 to 100% by mass, the rest 0 to 50% by mass is an arbitrary additional component, and said additional component is at least one kind selected from the group consisting of nonionic surfactants other than the above polyether-modified organopolysiloxane, anionic surfactants, animal and vegetable oils which are liquid at ordinary temperature, and water-soluble solid carriers.

(XX) The pest control composition according to the above-described (XIX), wherein any either or both of the nonionic surfactant or the anionic surfactant other than the above polyether-modified organopolysiloxane is 0 to 30% by mass based on the total amount of the composition, animal and vegetable oils which are liquid at ordinary temperature are 0 to 50% by mass, and the total of the above surfactant and the above animal and vegetable oils is 0 to 50% by mass.

(XXI) The pest control composition according to any one of the above-described (I) to (XVIII), wherein with regard to the content ratio of said polyglycerol fatty acid ester and said nonionic surfactant, said polyglycerol fatty acid ester has a ratio of 2 to 20 parts by mass based on 1 part by mass of said nonionic surfactant.

(XXII) The pest control composition according to the above-described (XXI), wherein the content ratio of said polyglycerol fatty acid ester is 2 to 10 parts by mass based on 1 part by mass of said nonionic surfactant.

(XXIII) The pest control composition according to any one of the above-described (I) to (XXII), wherein the formulation is an emulsion.

Preferable specific combination examples of said polyglycerol fatty acid ester and said nonionic surfactant in the present invention composition include the following ones. Specifically, a combination of decaglycerol decaoleic acid ester (HLB: about 4) and polyether-modified organopolysiloxane (HLB: about 14); a combination of decaglycerol decaoleic acid ester (HLB: about 4) and polyether-modified organopolysiloxane (HLB: about 14), and calcium stearoyl lactylate; a combination of decaglycerol erucic acid ester (HLB: about 4) and polyether-modified organopolysiloxane (HLB: about 14); a combination of decaglycerol erucic acid ester (HLB: about 4) and polyether-modified organopolysiloxane (HLB: about 14), and calcium stearoyl lactylate; a combination of polyglycerol-condensed ricinoleic acid ester (HLB: about 3) and polyether-modified organopolysiloxane (HLB: about 14); and a combination of polyglycerol-condensed ricinoleic acid ester (HLB: about 3) and polyether-modified organopolysiloxane (HLB: about 14), and calcium stearoyl lactylate can be included.

The method for manufacturing the pest control composition of the present invention will be described below, but not limited to this.

By putting a polyglycerol fatty acid ester which has an HLB of 5 or less and is liquid at ordinary temperature into a stirring furnace equipped with a stirring spring, adding said nonionic surfactant thereto, putting another arbitrary component if necessary, and uniformly mixing these raw materials, the pest control composition of the present invention can be prepared. In this regard, the addition order of the raw materials may be arbitrary. In addition, it is desired to heat to 30 to 100° C. and mix so that a uniform mixture is quickly prepared.

The present invention composition is usually used as an agrochemical formulation (emulsion) which is diluted with water to make a spray liquid in time of spraying. By spraying said spray liquid (hereinafter, which is referred to as the present invention spray liquid) in a sufficient amount onto the leaf surface of a plant parasitized by pests, the pests in crops for agriculture and horticulture can be controlled. The concentration of said polyglycerol fatty acid ester in said spray liquid is usually 300 to 2000 ppm and preferably approximately 300 to 1000 ppm. Said spray liquid can be obtained by diluting and adjusting the present invention composition with water so that the concentration of said polyglycerol fatty acid ester in said spray liquid is in the above-described range.

Specifically, the method for preparing the present invention spray liquid and the method for controlling pests will be explained below.

By adding 100 to 2000 parts by mass of water based on 1 part by mass of the present invention composition and well stirring to make a uniformly mixed liquid, the spray liquid can be obtained. By spraying said spray liquid in a sufficient amount onto pests or crops at which pests are emerging according to a common method using a hand spray, a shoulder atomizer, a power atomizer, a boom sprayer, a speed sprayer or the like, said pests can be controlled.

The pest control composition of the present invention controls in that the effective component directly acts on pests. Because aphids/spider mites and the like which are target pests of the present invention inhabit places which are difficult for a drug liquid to reach, such as the lower side of leaves, it is desired to spray in a sufficient amount on the lower and upper sides of leaves so that the spray liquid of the present invention is directly sprayed onto target pests.

The present invention composition, in spite of being a physically control mix, can also achieve the sufficient pest control effect as a spray liquid containing, as an effective component, said polyglycerol fatty acid ester at low concentration, as described above.

The pest control composition of the present invention is used for controlling pests emerging on agricultural crops such as fruit trees, tea plants, vegetables and ornamental flowers.

The pests targeted by the pest control composition of the present invention include, for example, mites, insects and the like doing harm to agricultural crops, which belong to the animal order such as Acarina, Hemiptera and Thysanoptera, and the composition has an excellent control effect particularly on spider mites and aphids. The organism belonging to Acarina includes spider mites, rust mites and broad mites. The spider mites include two-spotted spider mite, Kanzawa spider mite, citrus spider mite, apple spider mite and the like; the rust mites include tomato rust mite, citrus rust mite and the like; and the broad mites include tea broad mite and the like. The organism belonging to Hemiptera includes aphids, whiteflies, scale insects and the like. The aphids include cotton aphid, green peach aphid and the like; the whiteflies include greenhouse whitefly, sweetpotato whitefly and the like; and the scale insects include mulberry white scale insect and the like. The organism belonging to Thysanoptera includes western flower thrips, southern yellow thrips, tea yellow thrips and the like. In addition, the present invention composition is also effective for controlling disease damage due to funguses such as powdery mildew developing on vegetables, ornamental flowers and fruit trees.

When diluted with water and sprayed, the present invention composition achieves physical pest control through action of blocking the spiracle of target pests, and the like, by that said polyglycerol fatty acid ester adheres to the skin and shell surfaces of target pests, particularly around the spiracle. Therefore, the present invention composition has the equivalent control effect on a plural kinds of pests (for example, spider mites, aphids and the like) and also on pests in each stage of larvae, nymphs, adults and the like, and in addition, it can simultaneously control different kinds of pest species by one spray.

EXAMPLES

Hereinafter, the present invention will be more specifically explained with reference to the Examples. In this regard, in the present description, the Superscript® stands for a registered trademark.

Example 1

A pest control composition of the present invention was obtained by mixing 82.5 parts by mass of hexaglycerol pentaoleate (manufactured by Sakamoto Yakuhin Kogyo Co., Ltd.; trade name: SY Glyster PO-5S, HLB=4.9, esterification rate=62.5%) and 17.5 parts by mass of polyether-modified organopolysiloxane (manufactured by Shin-Etsu Chemical Co., Ltd.; trade name: KF-640, HLB=13.5, surface tension=21 mN/m).

Example 2

A pest control composition of the present invention was obtained by uniformly dissolving and mixing 80 parts by mass of hexaglycerol pentaoleate (manufactured by Sakamoto Yakuhin Kogyo Co., Ltd.; trade name: SY Glyster PO-5S, HLB=4.9, esterification rate=62.5%), 10 parts by mass of polyether-modified organopolysiloxane (manufactured by Shin-Etsu Chemical Co., Ltd.; trade name: KF-643, HLB=14, surface tension=21 mN/m), 7.5 parts by mass of polyether-modified organopolysiloxane (manufactured by Shin-Etsu Chemical Co., Ltd.; trade name: KF-351A, HLB=12, surface tension=26 mN/m) and 2.5 parts by mass of calcium stearoyl lactylate (manufactured by Musashino Chemical Laboratory, Ltd.; trade name: VERV) in a 40° C. hot-water tank.

Example 3

A pest control composition of the present invention was obtained by mixing 82.5 parts by mass of hexaglycerol pentaoleate (manufactured by Sakamoto Yakuhin Kogyo Co., Ltd.; trade name: SY Glyster PO-5S, HLB=4.9, esterification rate=62.5%), 10 parts by mass of polyether-modified organopolysiloxane (manufactured by Shin-Etsu Chemical Co., Ltd.; trade name: KF-643, HLB=14, surface tension=21 mN/m) and 7.5 parts by mass of polyether-modified organopolysiloxane (manufactured by Shin-Etsu Chemical Co., Ltd.; trade name: KF-351A, HLB=12, surface tension=26 mN/m).

Example 4

A pest control composition of the present invention was obtained by uniformly dissolving and mixing 86.5 parts by mass of hexaglycerol pentaoleate (manufactured by Sakamoto Yakuhin Kogyo Co., Ltd.; trade name: S Y Glyster PO-5S, HLB=4.9, esterification rate=62.5%), 7.5 parts by mass of polyether-modified organopolysiloxane (manufactured by Shin-Etsu Chemical Co., Ltd.; trade name: KF-643, HLB=14, surface tension=21 mN/m), 5 parts by mass of polyether-modified organopolysiloxane (manufactured by Shin-Etsu Chemical Co., Ltd.; trade name: KF-351A, HLB=12, surface tension=26 mN/m) and 1 part by mass of calcium stearoyl lactylate (manufactured by Musashino Chemical Laboratory, Ltd.; trade name: VERV) in a 40° C. hot-water tank.

Example 5

A pest control composition of the present invention was obtained by uniformly dissolving and mixing 84.5 parts by mass of hexaglycerol pentaoleate (manufactured by Sakamoto Yakuhin Kogyo Co., Ltd.; trade name: SY Glyster PO-5S, HLB=4.9, esterification rate=62.5%), 10 parts by mass of polyether-modified organopolysiloxane (manufactured by Shin-Etsu Chemical Co., Ltd.; trade name: KF-643, HLB=14, surface tension=21 mN/m), 5 parts by mass of polyether-modified organopolysiloxane (manufactured by Shin-Etsu Chemical Co., Ltd.; trade name: KF-351A, HLB=12, surface tension=26 mN/m) and 0.5 part by mass of calcium stearoyl lactylate (manufactured by Musashino Chemical Laboratory, Ltd.; trade name: VERV) in a 40° C. hot-water tank.

Example 6

A pest control composition of the present invention was obtained by mixing 75 parts by mass of hexaglycerol pentaoleate (manufactured by Sakamoto Yakuhin Kogyo Co., Ltd.; trade name: SY Glyster PO-5S, HLB=4.9, esterification rate=62.5%), 20 parts by mass of polyether-modified organopolysiloxane (manufactured by Shin-Etsu Chemical Co., Ltd.; trade name: KF-643, HLB=14, surface tension=21 mN/m) and 5 parts by mass of polyether-modified organopolysiloxane (manufactured by Shin-Etsu Chemical Co., Ltd.; trade name: KF-351A, HLB=12, surface tension=26 mN/m).

Example 7

A pest control composition of the present invention was obtained by mixing 70 parts by mass of hexaglycerol pentaoleate (manufactured by Sakamoto Yakuhin Kogyo Co., Ltd.; trade name: SY Glyster PO-5S, HLB=4.9, esterification rate=62.5%), 20 parts by mass of polyether-modified organopolysiloxane (manufactured by Shin-Etsu Chemical Co., Ltd.; trade name: KF-643, HLB=14, surface tension=21 mN/m) and 10 parts by mass of polyether-modified organopolysiloxane (manufactured by Shin-Etsu Chemical Co., Ltd.; trade name: KF-351A, HLB=12, surface tension=26 mN/m).

Example 8

A pest control composition of the present invention was obtained by mixing 82.5 parts by mass of hexaglycerol pentaoleate (manufactured by Sakamoto Yakuhin Kogyo Co., Ltd.; trade name: SY Glyster PO-5S, HLB=4.9, esterification rate=62.5%), 10 parts by mass of polyoxyethylene alkyl ether (manufactured by TOHO Chemical Industry Co., LTD.; trade name: Pegnol® ST-9, HLB=13, surface tension=30 mN/m) and 7.5 parts by mass of dioctyl sulfosuccinate (manufactured by Takemoto Oil & Fat Co., Ltd.; trade name: Newkalgen EP-70G, surface tension=28 mN/m).

Example 9

A pest control composition of the present invention was obtained by mixing 82.5 parts by mass of hexaglycerol pentaoleate (manufactured by Sakamoto Yakuhin Kogyo Co., Ltd.; trade name: SY Glyster PO-5S, HLB=4.9, esterification rate=62.5%), 10 parts by mass of polyether-modified organopolysiloxane (manufactured by Shin-Etsu Chemical Co., Ltd.; trade name: KF-643, HLB=14, surface tension=21 mN/m) and 7.5 parts by mass of polyoxyethylene alkyl ether (manufactured by TOHO Chemical Industry Co., LTD.; trade name: Pegnol® ST-9, HLB=13, surface tension=30 mN/m).

Example 10

A pest control composition of the present invention was obtained by mixing 82.5 parts by mass of hexaglycerol pentaoleate (manufactured by Sakamoto Yakuhin Kogyo Co., Ltd.; trade name: SY Glyster PO-5S, HLB=4.9, esterification rate=62.5%), 5 parts by mass of polyether-modified organopolysiloxane (manufactured by Shin-Etsu Chemical Co., Ltd.; trade name: KF-643, HLB=14, surface tension=21 mN/m), 2.5 parts by mass of polyether-modified organopolysiloxane (manufactured by Shin-Etsu Chemical Co., Ltd.; trade name: KF-351A, HLB=12, 26 mN/m), 5 parts by mass of polyoxyethylene alkyl ether (manufactured by TOHO Chemical Industry Co., LTD.; trade name: Pegnol® ST-9, HLB=13, surface tension=30 mN/m) and 5 parts by mass of dioctyl sulfosuccinate (manufactured by Takemoto Oil & Fat Co., Ltd.; trade name: Newkalgen EP-70G).

Example 11

A pest control composition of the present invention was obtained by mixing 35 parts by mass of hexaglycerol pentaoleate (manufactured by Sakamoto Yakuhin Kogyo Co., Ltd.; trade name: SY Glyster PO-5S, HLB=4.9, esterification rate=62.5%), 35 parts by mass of raw sesame oil (manufactured by Takemoto Oil & Fat Co., Ltd.; trade name Taihaku sesame oil), 10 parts by mass of polyether-modified organopolysiloxane (manufactured by Shin-Etsu Chemical Co., Ltd.; trade name: KF-643, HLB=14, surface tension=21 mN/m), 5 parts by mass of polyether-modified organopolysiloxane (manufactured by Shin-Etsu Chemical Co., Ltd.; trade name: KF-351A, HLB=12, surface tension=26 mN/m), and 15 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Example 12

A pest control composition of the present invention was obtained by uniformly dissolving and mixing 36.25 parts by mass of hexaglycerol pentaoleate (manufactured by Sakamoto Yakuhin Kogyo Co., Ltd.; trade name: SY Glyster PO-5S, HLB=4.9, esterification rate=62.5%), 36.25 parts by mass of raw sesame oil (manufactured by Takemoto Oil & Fat Co., Ltd.; trade name: Taihaku sesame oil), 10 parts by mass of polyether-modified organopolysiloxane (manufactured by Shin-Etsu Chemical Co., Ltd.; trade name: KF-643, HLB=14, surface tension=21 mN/m), 5 parts by mass of polyether-modified organopolysiloxane (manufactured by Shin-Etsu Chemical Co., Ltd.; trade name: KF-351A, HLB=12, surface tension=26 mN/m), 10 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m) and 2.5 parts by mass of calcium stearoyl lactylate (manufactured by Musashino Chemical Laboratory, Ltd.; trade name: VERV) in a 40° C. hot-water tank.

Example 13

A pest control composition of the present invention was obtained by mixing 42.5 parts by mass of hexaglycerol pentaoleate (manufactured by Sakamoto Yakuhin Kogyo Co., Ltd.; trade name: SY Glyster PO-5S, HLB=4.9, esterification rate=62.5%), 40 parts by mass of decaglycerol decaoleate (manufactured by Sakamoto Yakuhin Kogyo Co., Ltd.; trade name: SY Glyster DAO-7S, HLB=3.2, esterification rate=83.3%), 10 parts by mass of polyether-modified organopolysiloxane (manufactured by Shin-Etsu Chemical Co., Ltd.; trade name: KF-643, HLB=14, surface tension=21 mN/m) and 7.5 parts by mass of polyether-modified organopolysiloxane (manufactured by Shin-Etsu Chemical Co., Ltd.; trade name: KF-351A, HLB=12, surface tension=26 mN/m).

Example 14

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%) and 17.5 parts by mass of polyether-modified organopolysiloxane (manufactured by Shin-Etsu Chemical Co., Ltd.; trade name: KF-640, HLB=13.5, surface tension=21 mN/m).

Example 15

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%), 15 parts by mass of polyether-modified organopolysiloxane (manufactured by Shin-Etsu Chemical Co., Ltd.; trade name: KF-640, HLB=13.5, surface tension=21 mN/m) and 2.5 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Example 16

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%), 12.5 parts by mass of polyether-modified organopolysiloxane (manufactured by Shin-Etsu Chemical Co., Ltd.; trade name: KF-640, HLB=13.5, surface tension=21 mN/m) and 5 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Example 17

A pest control composition of the present invention was obtained by uniformly dissolving and mixing 80 parts by mass of decaglycerol decaoleate (manufactured by Sakamoto Yakuhin Kogyo Co., Ltd.; trade name: SY Glyster DAO-7S, HLB=3.2, esterification rate=83.3%), 10 parts by mass of polyether-modified organopolysiloxane (manufactured by Shin-Etsu Chemical Co., Ltd.; trade name: KF-643, HLB=14, surface tension=21 mN/m), 7.5 parts by mass of polyether-modified organopolysiloxane (manufactured by Shin-Etsu Chemical Co., Ltd.; trade name: KF-351A, HLB=12, surface tension=26 mN/m) and 2.5 parts by mass of calcium stearoyl lactylate (manufactured by Musashino Chemical Laboratory, Ltd.; trade name: VERV) in a 40° C. hot-water tank.

Example 18

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%), 10 parts by mass of polyether-modified organopolysiloxane (manufactured by Shin-Etsu Chemical Co., Ltd.; trade name: KF-643, HLB=14, surface tension=21 mN/m) and 7.5 parts by mass of polyether-modified organopolysiloxane (manufactured by Shin-Etsu Chemical Co., Ltd.; trade name: KF-351A, HLB=12, surface tension=26 mN/m).

Example 19

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%), 5 parts by mass of polyether-modified organopolysiloxane (manufactured by Shin-Etsu Chemical Co., Ltd.; trade name: KF-643, HLB=14, surface tension=21 mN/m) and 12.5 parts by mass of polyoxyethylene alkyl ether (manufactured by TOHO Chemical Industry Co., LTD.; trade name: Pegnol® ST-9, HLB=13, surface tension=30 mN/m).

Example 20

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%), 10 parts by mass of polyoxyethylene alkyl ether (manufactured by TOHO Chemical Industry Co., LTD.; trade name: Pegnol® ST-9, HLB=13, surface tension=30 mN/m) and 7.5 parts by mass of dioctyl sulfosuccinate (manufactured by Takemoto Oil & Fat Co., Ltd.; trade name: Newkalgen EP-70G).

Example 21

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%), 12.5 parts by mass of polyether-modified organopolysiloxane (manufactured by Shin-Etsu Chemical Co., Ltd.; trade name: KF-640, HLB=13.5, surface tension=21 mN/m) and 5 parts by mass of dioctyl sulfosuccinate (manufactured by Takemoto Oil & Fat Co., Ltd.; trade name: Newkalgen EP-70G).

Example 22

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%), 12.5 parts by mass of polyether-modified organopolysiloxane (manufactured by Shin-Etsu Chemical Co., Ltd.; trade name: KF-640, HLB=13.5, surface tension=21 mN/m) and 5 parts by mass of polyoxyethylene alkyl ether (manufactured by TOHO Chemical Industry Co., LTD.; trade name: Pegnol® ST-9, HLB=13, surface tension=30 mN/m).

Example 23

A pest control composition of the present invention was obtained by mixing 82.5 parts by mass of decaglycerol decaoleate (manufactured by Sakamoto Yakuhin Kogyo Co., Ltd.; trade name: SY Glyster DAO-7S, HLB=3.2, esterification rate=83.3%), 7.5 parts by mass of polyether-modified organopolysiloxane (manufactured by Shin-Etsu Chemical Co., Ltd.; trade name: KF-640, HLB=13.5, surface tension=21 mN/m), 5 parts by mass of dioctyl sulfosuccinate (manufactured by Takemoto Oil & Fat Co., Ltd.; trade name: Newkalgen EP-70G) and 5 parts by mass of polyoxyethylene alkyl ether (manufactured by TOHO Chemical Industry Co., LTD.; trade name: Pegnol® ST-9, HLB=13, surface tension=30 mN/m).

Example 24

A pest control composition of the present invention was obtained by mixing 35 parts by mass of decaglycerol decaoleate (manufactured by Sakamoto Yakuhin Kogyo Co., Ltd.; trade name: SY Glyster DAO-7S, HLB=3.2, esterification rate=83.3%), 35 parts by mass of raw sesame oil (manufactured by Takemoto Oil & Fat Co., Ltd.; trade name: Taihaku sesame oil), 10 parts by mass of polyether-modified organopolysiloxane (manufactured by Shin-Etsu Chemical Co., Ltd.; trade name: KF-643, HLB=14, surface tension 21 mN/m), 5 parts by mass of polyether-modified organopolysiloxane (manufactured by Shin-Etsu Chemical Co., Ltd.; trade name: KF-351A, HLB=12, surface tension=26 mN/m) and 15 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Example 25

A pest control composition of the present invention was obtained by mixing 80 parts of decaglycerol erucate (manufactured by Sakamoto Yakuhin Kogyo Co., Ltd.; trade name: SY Glyster NE-750, HLB=3.2), 10 parts by mass of polyether-modified organopolysiloxane (manufactured by Shin-Etsu Chemical Co., Ltd.; trade name: KF-643, HLB=14, surface tension=21 mN/m), 7.5 parts by mass of polyether-modified organopolysiloxane (manufactured by Shin-Etsu Chemical Co., Ltd.; trade name: KF-351A, HLB=12, surface tension=26 mN/m) and 2.5 parts by mass of calcium stearoyl lactylate (manufactured by Musashino Chemical Laboratory, Ltd.; trade name: VERV).

Example 26

A pest control composition of the present invention was obtained by mixing 82.5 parts of decaglycerol erucate (manufactured by Sakamoto Yakuhin Kogyo Co., Ltd.; trade name: SY Glyster NE-750, HLB=3.2), 10 parts by mass of polyether-modified organopolysiloxane (manufactured by Shin-Etsu Chemical Co., Ltd.; trade name: KF-643, HLB=14, surface tension=21 mN/m) and 7.5 parts by mass of polyether-modified organopolysiloxane (manufactured by Shin-Etsu Chemical Co., Ltd.; trade name: KF-351A, HLB=12, surface tension=26 mN/m).

Example 27

A pest control composition of the present invention was obtained by mixing 35 parts of decaglycerol erucate (manufactured by Sakamoto Yakuhin Kogyo Co., Ltd.; trade name: SY Glyster NE-750, HLB=3.2), 35 parts by mass of raw sesame oil manufactured by Takemoto Oil & Fat Co., Ltd.; trade name: Taihaku sesame oil), 10 parts by mass of polyether-modified organopolysiloxane (manufactured by Shin-Etsu Chemical Co., Ltd.; trade name: KF-643, HLB=14, surface tension=21 mN/m), 5 parts by mass of polyether-modified organopolysiloxane (manufactured by Shin-Etsu Chemical Co., Ltd.; trade name: KF-351A, HLB=12, surface tension=26 mN/m) and 15 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Example 28

A pest control composition of the present invention was obtained by mixing 82.5 parts of decaglycerol erucate (manufactured by Sakamoto Yakuhin Kogyo Co., Ltd.; trade name: SY Glyster OE-750, HLB=3.7) and 17.5 parts of polyether-modified organopolysiloxane (manufactured by Shin-Etsu Chemical Co., Ltd.; trade name: KF-351A, HLB=14.5, surface tension=26 mN/m).

Example 29

A pest control composition of the present invention was obtained by uniformly dissolving and mixing 80 parts of decaglycerol erucate (manufactured by Sakamoto Yakuhin Kogyo Co., Ltd.; trade name: SY Glyster OE-750, HLB=3.7), 10 parts by mass of polyether-modified organopolysiloxane (manufactured by Shin-Etsu Chemical Co., Ltd.; trade name: KF-643, HLB=14, surface tension=21 mN/m), 7.5 parts of polyether-modified organopolysiloxane (manufactured by Shin-Etsu Chemical Co., Ltd.; trade name: KF-351A, HLB=14.5, surface tension=26 mN/m) and 2.5 parts by mass of calcium stearoyl lactylate (manufactured by Musashino Chemical Laboratory, Ltd.; trade name: VERV) in a 40° C. hot-water tank.

Example 30

A pest control composition of the present invention was obtained by mixing 82.5 parts of decaglycerol erucate (manufactured by Sakamoto Yakuhin Kogyo Co., Ltd.; trade name: SY Glyster OE-750, HLB=3.7), 10 parts by mass of polyether-modified organopolysiloxane (manufactured by Shin-Etsu Chemical Co., Ltd.; trade name: KF-643, HLB=14, surface tension=21 mN/m) and 7.5 parts of polyether-modified organopolysiloxane (manufactured by Shin-Etsu Chemical Co., Ltd.; trade name: KF-351A, HLB=14.5, surface tension=26 mN/m).

Example 31

A pest control composition of the present invention was obtained by mixing 35 parts of decaglycerol erucate (manufactured by Sakamoto Yakuhin Kogyo Co., Ltd.; trade name: SY Glyster OE-750, HLB=3.7), 35 parts by mass of raw sesame oil (manufactured by Takemoto Oil & Fat Co., Ltd.; trade name: Taihaku sesame oil), 10 parts by mass of polyether-modified organopolysiloxane (manufactured by Shin-Etsu Chemical Co., Ltd.; trade name: KF-643, HLB=14, surface tension=21 mN/m), 5 parts by mass of polyether-modified organopolysiloxane (manufactured by Shin-Etsu Chemical Co., Ltd.; trade name: KF-351A, HLB=12, surface tension=26 mN/m) and 15 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Example 32

A pest control composition of the present invention was obtained by mixing 82.5 parts of hexaglycerol condensed ricinoleate (manufactured by Sakamoto Yakuhin Kogyo Co., Ltd.; trade name: SY Glyster CR-500, HLB=3) and 17.5 parts of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Example 33

A pest control composition of the present invention was obtained by uniformly dissolving and mixing 80 parts by mass of polyglycerol condensed ricinoleate (manufactured by Sakamoto Yakuhin Kogyo Co., Ltd.; trade name: SY Glyster CRS-75, HLB=3), 10 parts by mass of polyether-modified organopolysiloxane (manufactured by Shin-Etsu Chemical Co., Ltd.; trade name: KF-643, HLB=14, surface tension=21 mN/m), 7.5 parts by mass of polyether-modified organopolysiloxane (manufactured by Shin-Etsu Chemical Co., Ltd.; trade name: KF-351A, HLB=12, surface tension=26 mN/m) and 2.5 parts by mass of calcium stearoyl lactylate (manufactured by Musashino Chemical Laboratory, Ltd.; trade name: VERV) in a 40° C. hot-water tank.

Example 34

A pest control composition of the present invention was obtained by mixing 82.5 parts by mass of polyglycerol condensed ricinoleate (manufactured by Sakamoto Yakuhin Kogyo Co., Ltd.; trade name: SY Glyster CRS-75, HLB=3), 10 parts by mass of polyether-modified organopolysiloxane (manufactured by Shin-Etsu Chemical Co., Ltd.; trade name: KF-643, HLB=14, surface tension 21 mN/m) and 7.5 parts by mass of polyether-modified organopolysiloxane (manufactured by Shin-Etsu Chemical Co., Ltd.; trade name: KF-351A, HLB=12, surface tension 26 mN/m).

Example 35

A pest control composition of the present invention was obtained by mixing 35 parts by mass of polyglycerol condensed ricinoleate (manufactured by Sakamoto Yakuhin Kogyo Co., Ltd.; trade name: SY Glyster CRS-75, HLB=3), 35 parts by mass of raw sesame oil (manufactured by Takemoto Oil & Fat Co., Ltd.; trade name: Taihaku sesame oil), 10 parts by mass of polyether-modified organopolysiloxane (manufactured by Shin-Etsu Chemical Co., Ltd.; trade name: KF-643, HLB=14, surface tension=21 mN/m), 5 parts by mass of polyether-modified organopolysiloxane (manufactured by Shin-Etsu Chemical Co., Ltd.; trade name: KF-351A, HLB=12, surface tension=26 mN/m) and 15 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Example 36

A pest control composition of the present invention was obtained by mixing 32.5 parts by mass of polyglycerol condensed ricinoleate (manufactured by Sakamoto Yakuhin Kogyo Co., Ltd.; trade name: SY Glyster CRS-75, HLB=3), 35 parts by mass of raw sesame oil (manufactured by Takemoto Oil & Fat Co., Ltd.; trade name: Taihaku sesame oil), 10 parts by mass of polyether-modified organopolysiloxane (manufactured by Shin-Etsu Chemical Co., Ltd.; trade name: KF-643, HLB=14, surface tension=21 mN/m), 5 parts by mass of polyether-modified organopolysiloxane (manufactured by Shin-Etsu Chemical Co., Ltd.; trade name: KF-351A, HLB=12, surface tension=26 mN/m), 15 parts by mass of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m) and 2.5 parts by mass of calcium stearoyl lactylate (manufactured by Musashino Chemical Laboratory, Ltd.; trade name: VERV), and by uniformly dissolving the mixture in a 40° C. hot-water tank.

Comparative Example 1

A comparative example composition was obtained by mixing 82.5 parts of hexaglycerol monooleate (manufactured by Sakamoto Yakuhin Kogyo Co., Ltd.; trade name: SY Glyster MO-5S, HLB=11.6) and 17.5 parts of tap water.

Comparative Example 2

A comparative example composition was obtained by mixing 82.5 parts of decaglycerol monocaprate (manufactured by Sakamoto Yakuhin Kogyo Co., Ltd.; trade name: SY Glyster MCA-750, HLB=16) and 17.5 parts of tap water.

Comparative Example 3

A comparative example composition was obtained by mixing 82.5 parts of diglycerol monooleate (manufactured by Sakamoto Yakuhin Kogyo Co., Ltd.; trade name: S-FACE O-201P, HLB=8) and 17.5 parts of a mixture of polyoxyethylene styrylphenyl ether and sodium dodecylbenzenesulfonate (manufactured by TOHO Chemical Industry Co., LTD.; trade name: Sorpol® 355, HLB=11, surface tension=32 mN/m).

Comparative Example 4

A comparative example composition was obtained by mixing 80 parts by mass of tetraglycerol monolaurate (manufactured by Sakamoto Yakuhin Kogyo Co., Ltd.; trade name: SY Glyster ML-310, HLB=10.3), 10 parts by mass of polyether-modified organopolysiloxane (manufactured by Shin-Etsu Chemical Co., Ltd.; trade name: KF-643, HLB=14, surface tension=21 mN/m), 7.5 parts by mass of polyether-modified organopolysiloxane (manufactured by Shin-Etsu Chemical Co., Ltd.; trade name: KF-351A, HLB=12, surface tension=26 mN/m) and 2.5 parts by mass of calcium stearoyl lactylate (manufactured by Musashino Chemical Laboratory, Ltd.; trade name: VERV).

Comparative Example 5

A comparative example composition was obtained by mixing 82.5 parts by mass of tetraglycerol monolaurate (manufactured by Sakamoto Yakuhin Kogyo Co., Ltd.; trade name: SY Glyster ML-310, HLB=10.3), 10 parts by mass of polyether-modified organopolysiloxane (manufactured by Shin-Etsu Chemical Co., Ltd.; trade name: KF-643, HLB=14, surface tension=21 mN/m) and 7.5 parts by mass of polyether-modified organopolysiloxane (manufactured by Shin-Etsu Chemical Co., Ltd.; trade name: KF-351A, HLB=12, surface tension=26 mN/m).

Comparative Example 6

A commercially available liquid formulation, Nenchaku-Kun® (which is a trade name and manufactured by Sumitomo Chemical Co., Ltd.; hydroxypropyl starch 5%), was used as a composition of Comparative Example 6.

Comparative Example 7

A commercially available emulsion, Sun Crystal® (which is a trade name and manufactured by Sankei Chemical Co., Ltd.; fatty acid glyceride 90%), was used as a composition of Comparative Example 7.

Comparative Example 8

A commercially available liquid formulation, Ecopita® (which is a trade name and manufactured by Kyoyu Agri Co., Ltd.; reduced starch saccharide 60%), was used as a composition of Comparative Example 8.

Comparative Example 9

A commercially available emulsion, Akaritacchi® (which is a trade name and manufactured by Ishihara Bioscience Co., Ltd.; propylene glycol mono-fatty acid ester emulsion: 70%, polyoxyethylene alkyl ether: 9%), was used as a composition of Comparative Example 9.

Test Example 1

A piece of kidney bean leaf parasitized by two-spotted spider mites was placed on an eggplant leaf at the fifth leaf stage to settle the two-spotted spider mites on eggplants. After confirming settlement of the two-spotted spider mites, the number of adults of the parasitizing two-spotted spider mites was measured. Each of the compositions obtained in Examples and the compositions obtained in Comparative Examples was diluted 1000 times to prepare a spray liquid, and a sufficient amount (about 100 mL/plant) of the spray liquid was sprayed onto the eggplants. In addition, each composition of Comparative Example 6 to Comparative Example 8 was diluted at the registered concentration of each commercially available formulation for spider mites to make a spray liquid, which was likewise sprayed onto the eggplants. After spraying, the eggplants were left to stand in a constant temperature room at 25° C., and 5 days later, the number of surviving adults was measured. For comparison, two-spotted spider mites were settled on the eggplants and left to stand for 5 days without spray treatment, before and after which the number of surviving adults of the two-spotted spider mites was measured. By the following calculation formula, a corrected density index when using each composition of Examples and Comparative Examples was determined, and the results are summarized in Table 1.

Corrected density index=(Number of adults after treatment in treatment area/Number of adults before treatment in treatment area)×(Number of adults before treatment in non-treatment area/Number of adults after treatment in non-treatment area)×100

TABLE 1

Result list of Test Example 1

| Sample | Treatment concentration (times dilution) | Number of adults before treatment | Number of adults 5 days after treatment | Corrected density index |
|---|---|---|---|---|
| Example 1 | 1000 | 45 | 4 | 6.8 |
| Example 2 | 1000 | 39 | 2 | 3.9 |
| Example 3 | 1000 | 40 | 2 | 3.8 |
| Example 4 | 1000 | 83 | 13 | 12.0 |
| Example 5 | 1000 | 78 | 12 | 11.8 |
| Example 6 | 1000 | 62 | 1 | 1.2 |
| Example 7 | 1000 | 58 | 6 | 7.9 |
| Example 14 | 1000 | 63 | 0 | 0.0 |
| Example 15 | 1000 | 67 | 11 | 12.6 |
| Example 16 | 1000 | 74 | 7 | 7.2 |
| Example 18 | 1000 | 34 | 1 | 2.3 |
| Example 23 | 1000 | 57 | 8 | 10.8 |
| Example 25 | 1000 | 42 | 1 | 1.8 |
| Example 26 | 1000 | 40 | 1 | 1.9 |
| Example 28 | 1000 | 57 | 7 | 9.4 |
| Example 29 | 1000 | 39 | 4 | 7.9 |
| Example 30 | 1000 | 55 | 6 | 8.4 |
| Comp. Exam. 1 | 1000 | 55 | 28 | 39.0 |

TABLE 1-continued

Result list of Test Example 1

| Sample | Treatment concentration (times dilution) | Number of adults before treatment | Number of adults 5 days after treatment | Corrected density index |
|---|---|---|---|---|
| Comp. Exam. 2 | 1000 | 45 | 31 | 52.8 |
| Comp. Exam. 4 | 1000 | 39 | 30 | 59.0 |
| Comp. Exam. 5 | 1000 | 39 | 29 | 57.0 |
| Comp. Exam. 6 | 100 | 69 | 9 | 10.0 |
|  | 1000 | 102 | 44 | 33.1 |
| Comp. Exam. 7 | 300 | 82 | 9 | 8.4 |
|  | 1000 | 81 | 58 | 54.9 |
| Comp. Exam. 8 | 100 | 116 | 31 | 20.5 |
|  | 1000 | 93 | 53 | 43.7 |
| Comp. Exam. 9 | 1000 | 94 | 19 | 15.5 |
| Non-treatment |  | 82 | 107 | 100.0 |

Comp. Exam.: Comparative Example

As a result of Test Example 1, the composition of each Example of the present invention showed an extremely high control effect on two-spotted spider mites in application of a 1000 times diluent with water, compared with application at the same concentration of each composition of Comparative Examples 1 to 5. In addition, compared with the 100 times diluents of Comparative Examples 6 and 8, the 300 times diluent of Comparative Example 7 and the 1000 times diluent of Comparative Example 9, which have been already registered as an agrochemical and applied actually for small pest control, the 1000 times diluent of each Example composition of the present invention showed an equivalent or higher control effect. In addition, each Example composition of the present invention showed an extremely high control effect, compared with the 1000 times diluents from Comparative Example 6 to 8.

Test Example 2

Adults of the cotton aphid were released on cucumbers at the third leaf stage to settle the cotton aphid. After confirming the increased density of the cotton aphid, the numbers of parasitizing adults and larvae of the cotton aphid were measured. Each of the compositions obtained in Examples and the compositions obtained in Comparative Examples was diluted 1000 times to prepare a spray liquid, and a sufficient amount (100 mL/plant) of the spray liquid was sprayed onto the cucumbers. In addition, each composition of Comparative Example 6 to Comparative Example 8 was diluted at the registered concentration of each commercially available formulation for aphids to make a spray liquid, which was likewise sprayed onto the cucumbers. After spraying the composition, the cucumbers were left to stand in a constant temperature room at 25° C., and 2 days later, the number of surviving insects (adults and larvae) was measured. For comparison, cotton aphids were settled on cucumbers and left to stand for 2 days without spray treatment, before and after which the number of surviving cotton aphids was measured. By the following calculation formula, a corrected density index when using each composition of Examples and Comparative Examples was determined, and the results are summarized in Table 2.

Corrected density index=(Number of insects after treatment in treatment area/Number of insects before treatment in treatment area)×(Number of insects before treatment in non-treatment area/Number of insects after treatment in non-treatment area)×100

TABLE 2

Result list of Test Example 2

| Sample | Treatment concentration (times dilution) | Number of insects before treatment | Number of insects 2 days after treatment | Corrected density index |
|---|---|---|---|---|
| Example 1 | 1000 | 102 | 50 | 19.1 |
| Example 2 | 1000 | 225 | 19 | 3.3 |
| Example 3 | 1000 | 32 | 8 | 9.8 |
| Example 11 | 1000 | 150 | 74 | 19.3 |
| Example 14 | 1000 | 132 | 3 | 0.9 |
| Example 15 | 1000 | 56 | 28 | 19.5 |
| Example 16 | 1000 | 116 | 49 | 16.5 |
| Example 17 | 1000 | 303 | 3 | 0.4 |
| Example 18 | 1000 | 64 | 18 | 11.0 |
| Example 19 | 1000 | 23 | 4 | 6.8 |
| Example 22 | 1000 | 50 | 22 | 17.2 |
| Example 25 | 1000 | 174 | 8 | 1.8 |
| Example 28 | 1000 | 109 | 37 | 13.3 |
| Example 29 | 1000 | 150 | 2 | 0.5 |
| Example 30 | 1000 | 182 | 63 | 13.5 |
| Example 31 | 1000 | 180 | 68 | 14.8 |
| Example 33 | 1000 | 163 | 5 | 1.2 |
| Example 35 | 1000 | 149 | 42 | 11.0 |
| Comp. Exam. 2 | 1000 | 95 | 125 | 51.4 |
| Comp. Exam. 3 | 1000 | 124 | 144 | 52.8 |
| Comp. Exam. 6 | 100 | 126 | 130 | 40.3 |
|  | 1000 | 98 | 153 | 64.3 |
| Comp. Exam. 7 | 300 | 61 | 4 | 2.6 |
|  | 1000 | 113 | 106 | 36.6 |
| Comp. Exam. 8 | 100 | 75 | 8 | 4.2 |
|  | 1000 | 86 | 141 | 64.0 |
| Comp. Exam. 9 | 1000 | 130 | 226 | 67.9 |
| Non-treatment area | — | 91 | 233 | 100.0 |

Comp. Exam.: Comparative Example

As a result of Test Example 2, in application of a 1000 times diluent with water, the composition of each Example of the present invention showed an extremely high control effect on cotton aphids, compared with application of a 1000 times diluent of each composition of Comparative Examples 2, 3 and 6 to 9. In addition, the 1000 times diluent of each Example composition of the present invention also showed an extremely high control effect, compared with the 100 times diluent from Comparative Example 6 which has been already registered as an agrochemical and applied actually for small pest control.

As shown in Test Example 1 and Test Example 2, each composition using a polyglycerol fatty acid ester with an HLB of 6 or more in Comparative Examples 1 to 5 had a low pest control effect, unlike Example compositions of the present invention using the polyglycerol fatty acid ester of the present invention. The reason for this result is unclear, but it is inferred that the polyglycerol fatty acid ester of the present invention exhibits special affinity to the skin and shell of pests and thus blocks the spiracle of pests to suffocate to death.

In addition, the composition of Comparative Example 9 showed a high control effect on two-spotted spider mites in application of a 1000 times dilution while it had a low control effect on the cotton aphids at the same concentration, and thus it was found to have difference in control effect between target pests. Therefore, it is considered that the composition of Comparative Example 9 has difficulty in simultaneously controlling two-spotted spider mites and cotton aphids by spraying a 1000 times diluent. In contrast to this, Example compositions of the present application showed a satisfying control effect on the pests with a 1000 times diluent with water. Further, it was confirmed that Example compositions have almost no difference in control effect between two-spotted spider mites and cotton aphids and can simultaneously control these plural target pests by one spray of a 1000 times diluent. That is, the pest control composition of the present application has a significant pest control effect and also can achieve labor-saving of spray operation.

Test Example 3

Each composition of Examples and Comparative Examples was diluted at a concentration shown in the below-described Table 3 to prepare a spray liquid, and a sufficient amount (about 100 mL/plant) of the spray liquid was sprayed onto strawberries (breed: Tochiotome, immediately before anthesis) and eggplants (breed: Senryo 2-Go, nursery plant at the eighth leaf stage). Seven days after spraying, chemical injury (existence or non-existence of spotting or discoloration on leaf) of each crop was researched. The results are shown in Table 3.

TABLE 3

Result list of Test Example 3

| Sample | Treatment concentration (times dilution) | Strawberry | Eggplant |
| --- | --- | --- | --- |
| Example 2 | 500 | – | – |
| | 1000 | – | – |
| Example 3 | 500 | – | – |
| | 1000 | – | – |
| Example 6 | 500 | – | – |
| | 1000 | – | – |
| Example 14 | 500 | – | – |
| | 1000 | – | – |
| Comparative Example 9 | 500 | + | + |
| | 1000 | + | – |

Evaluation criteria: No change on leaf: –; Spotting or discoloration observed on leaf: +.

From the results of Test Example 3, it was confirmed that the compositions of Examples of the present application have low risk of chemical injury compared with that of the Comparative Example 9 because chemical injury to the strawberries and the eggplants thereby was not found.

Test Example 4

Each composition of Examples 1, 14, 16 and 28 and Comparative Examples 3 and 9 was diluted 1000 times with water to prepare a spray liquid, and each spray liquid was sprayed onto the adults of the cotton aphids parasitizing the cucumber leaf. After spraying, with a microscope (manufactured by Keyence; trade name: Microscope VHX-200), the adhesion state of said composition to the cotton aphids was researched. The adhesion state of each composition to the insect body was evaluated with a 5 scale index. Their adherence index evaluation results are shown in Table 4.

TABLE 4

Result list of Test Example 4

| Sample | Treatment concentration (times dilution) | Adherence index |
| --- | --- | --- |
| Example 1 | 1000 | 4 |
| Example 14 | 1000 | 5 |
| Example 16 | 1000 | 5 |
| Example 28 | 1000 | 5 |

TABLE 4-continued

Result list of Test Example 4

| Sample | Treatment concentration (times dilution) | Adherence index |
| --- | --- | --- |
| Comparative Example 3 | 1000 | 1 |
| Comparative Example 9 | 1000 | 2 |

Evaluation criteria: adherence index
1: Adhesion of oil droplets is hardly observed.
2: Adhesion of small oil droplets is slightly observed.
3: Adhesion of many small oil droplets is observed.
4: With small oil droplets, adhesion of big oil droplet particles is observed.
5: Adhesion of many big oil droplets is observed.

From the results of Test Example 4, it was confirmed that in the test using the compositions of Examples 1, 14, 16 and 28, many oil droplets aggregated and adhered around the body surface of the cotton aphids. On the other hand, it was confirmed by observation that in the test using the compositions of Comparative Examples 3 and 9, adhesion of oil droplets to the skin and shell of the target insect pest was less. It was found by observation of the target insect pest sprayed with a water-diluted liquid that the Example compositions of the present application showed good adhesion properties of the effective component to the skin and shell of the insect pest. With such phenomenon, it is inferred that the present invention composition shows a high control effect on pests such as spider mites and aphids even by a spray liquid with low concentration.

INDUSTRIAL APPLICABILITY

The pest control composition of the present invention has an action leading small pests to death by spraying a spray liquid prepared by diluting with water. Therefore, the pest control composition of the present invention is utilized as an agrochemical composition for controlling harmful small organisms in agricultural and horticultural plants. The pest control composition of the present invention has a polyglycerol fatty acid ester ensuring safety to the human body as an effective component and shows a sufficient pest control effect in application at low concentration. In addition, the pest control composition of the present invention has less difference in control effect between pest species, so it can be applied to various target organisms and also utilized as an agrochemical for agricultural and horticultural pest control, which allows simultaneous control of plural kinds of target organisms by one application.

The invention claimed is:
1. A pest control composition consisting of
   a pest-controlling effective amount of an active component that consists of a polyether-modified organopolysiloxane as a nonionic surfactant and at least one polyglycerol fatty acid ester having an HLB of 5 or less selected from the group consisting of hexaglycerol pentaoleate, decaglycerol decaoleate, decaglycerol erucate and polyglycerol condensed ricinoleate; and
   at least one additional component selected from the group consisting of anionic surfactants, raw sesame seed oil, sesame oil, soybean oil, rapeseed oil, water-soluble solid carriers, and nonionic surfactants other than said polyether-modified organopolysiloxane.
2. The pest control composition according to claim 1, wherein the polyether-modified organopolysiloxane nonionic surfactant is a nonionic surfactant having a surface tension (20° C.) of 30 mN/m or less and an HLB of 13 or more in a 0.1% by mass aqueous solution.

3. The pest control composition according to claim 1, wherein the content of the polyglycerol fatty acid ester is 30 to 98% by mass and the content of the polyether-modified organopolysiloxane nonionic surfactant is 2 to 30% by mass in the composition.

4. The pest control composition according to claim 1, wherein the pest is one or more organisms belonging to an animal order selected from the group consisting of Acarina, Hemiptera and Thysanoptera.

5. A spray liquid obtained by diluting the pest control composition according to claim 1 with water.

6. A method for controlling a pest, consisting of directly spraying the spray liquid according to claim 5 onto a pest or a crop at which a pest is emerging.

7. The method for controlling a pest according to claim 6, where the polyglycerol fatty acid ester concentration in said spray liquid is 300 to 2000 ppm.

8. The method for controlling a pest according to claim 6, wherein the pest is one or more organisms belonging to an animal order selected from the group consisting of Acarina, Hemiptera and Thysanoptera.

9. The pest control composition according to claim 1, wherein the polyether-modified organopolysiloxane nonionic surfactant is a nonionic surfactant having an HLB of 12 or more and a surface tension of 30 mN/m or less at 20° C. in a 0.1% by mass solution; the content of said polyglycerol fatty acid ester is 30 to 98% by mass; the content of said polyether-modified organopolysiloxane nonionic surfactant is 2 to 40% by mass; and the pest is a pest in agriculture and horticulture.

10. The pest control composition according to claim 1, wherein the polyether-modified organopolysiloxane nonionic surfactant has an HLB of 12 or more and its content is 2 to 35% by mass.

11. A pest control composition consisting of a pest-controlling effective amount of a polyether-modified organopolysiloxane as a nonionic surfactant and a polyglycerol fatty acid ester having an HLB of 5 or less selected from the group consisting of hexaglycerol pentaoleate, decaglycerol decaoleate, decaglycerol erucate and polyglycerol condensed ricinoleate.

12. The pest control composition according to claim 11, wherein the polyether-modified organopolysiloxane nonionic surfactant is a nonionic surfactant having a surface tension (20° C.) of 30 mN/m or less and an HLB of 13 or more in a 0.1% by mass aqueous solution.

13. The pest control composition according to claim 11, wherein the pest is one or more organisms belonging to an animal order selected from the group consisting of Acarina, Hemiptera and Thysanoptera.

14. A spray liquid obtained by diluting the pest control composition according to claim 11 with water.

15. A method for controlling a pest, consisting of directly spraying the spray liquid according to claim 14 onto a pest or a crop at which a pest is emerging.

16. The method for controlling a pest according to claim 15, wherein the polyglycerol fatty acid ester concentration in said spray liquid is 300 to 2000 ppm.

17. The method for controlling a pest according to claim 15, wherein the pest is one or more organisms belonging to an animal order selected from the group consisting of Acarina, Hemiptera and Thysanoptera.

18. A method for controlling a pest consisting of
directly spraying a pest control composition consisting of
a pest-controlling effective amount of an active component that consists of a polyether-modified organopolysiloxane as a nonionic surfactant and at least one polyglycerol fatty acid ester having and HLB of 5 or less selected from the group consisting of hexaglycerol pentaoleate, decaglycerol decaoleate, decaglycerol erucate and polyglycerol condensed ricinoleate; and
at least one additional component selected from the group consisting of anionic surfactants, raw sesame seed oil, sesame oil, soybean oil, rapeseed oil, water-soluble solid carriers, and nonionic surfactants other than said polyether-modified organopolysiloxane onto a pest or a crop at which a pest is emerging.

19. The method for controlling a pest according to claim 18, wherein the polyglycerol fatty acid ester concentration in said spray liquid is 300 to 2000 ppm.

20. The method of controlling a pest according to claim 18 or 19, wherein the pest is one or more organisms belonging to an animal order selected from the group consisting of Acarina, Hemiptera and Thysanoptera.

* * * * *